US009895367B2

(12) United States Patent
Parvataneni et al.

(10) Patent No.: US 9,895,367 B2
(45) Date of Patent: Feb. 20, 2018

(54) FORMULATION COMPRISING PHENYLAMINOPYRIMIDINE DERIVATIVE AS ACTIVE AGENT

(75) Inventors: Durga Maheswari Parvataneni, Andhra Pradesh (IN); Siddhartha Yedluri, Andhra Pradesh (IN); Venkata Satyanarayana Appadwedula, Andhra Pradesh (IN); Kali Satya Bhujanga Rao, Andhra Pradesh (IN); Venkaiah Chowdary Nannapaneni, Andhra Pradesh (IN)

(73) Assignee: NATCO PHARMA LIMITED, Hyderabad (IN)

( * ) Notice: Subject to any disclaimer, the term of this patent is extended or adjusted under 35 U.S.C. 154(b) by 61 days.

(21) Appl. No.: 14/003,445

(22) PCT Filed: Aug. 10, 2011

(86) PCT No.: PCT/IB2011/001842
§ 371 (c)(1),
(2), (4) Date: Sep. 5, 2013

(87) PCT Pub. No.: WO2012/120328
PCT Pub. Date: Sep. 13, 2012

(65) Prior Publication Data
US 2013/0338180 A1 Dec. 19, 2013

(30) Foreign Application Priority Data
Mar. 7, 2011 (GB) .................................. 1103860.1

(51) Int. Cl.
| A61K 31/506 | (2006.01) |
| A61K 9/107 | (2006.01) |
| A61K 9/00 | (2006.01) |
| A61K 9/48 | (2006.01) |
| A61K 47/10 | (2017.01) |
| A61K 47/14 | (2017.01) |
| A61K 9/08 | (2006.01) |
| A61K 47/44 | (2017.01) |

(52) U.S. Cl.
CPC .......... *A61K 31/506* (2013.01); *A61K 9/0053* (2013.01); *A61K 9/08* (2013.01); *A61K 9/107* (2013.01); *A61K 9/4858* (2013.01); *A61K 9/4866* (2013.01); *A61K 47/10* (2013.01); *A61K 47/14* (2013.01); *A61K 47/44* (2013.01)

(58) Field of Classification Search
None
See application file for complete search history.

(56) References Cited

U.S. PATENT DOCUMENTS

| 5,645,856 A * | 7/1997 | Lacy et al. .................... 424/455 |
| 2004/0224967 A1 | 11/2004 | Chen | |
| 2007/0232633 A1 | 10/2007 | Kompella et al. | |
| 2008/0207904 A1 * | 8/2008 | MacDonald et al. ......... 544/364 |
| 2008/0274173 A1 * | 11/2008 | Sill et al. ...................... 424/450 |
| 2008/0306100 A1 | 12/2008 | Kompella et al. | |
| 2009/0227611 A1 | 9/2009 | Kompella et al. | |
| 2009/0291981 A1 * | 11/2009 | Schaab ................ C07D 401/14 514/333 |
| 2010/0240672 A1 * | 9/2010 | Breitenbach et al. ... 514/252.18 |

FOREIGN PATENT DOCUMENTS

| WO | 99/06024 | 2/1999 |
| WO | 00/51571 A2 | 9/2000 |
| WO | 2005/014048 A1 | 2/2005 |
| WO | 2006/027795 A1 | 3/2006 |
| WO | 2009/109867 A2 | 9/2009 |
| WO | 2009/109867 A3 | 9/2009 |

OTHER PUBLICATIONS

Gursoy et al. (Biomedicine & Pharmacotherapy 58 (2004) 173-182).*
Florence et al. (Physicochemical Principles of Pharmacy, 6th Edition, p. 235, Pharmaceutical Press 2016).*
Mullertz et al. (Journal of Pharmacy and Pharmacology, 2010; 62: 1622-1636).*
Gondi, Christopher S. et al., "Antitumor activity of NRC-AN-019 in a pre-clinical breast cancer model," *International Journal of Oncology* (2011), 39:641-648.
Nanjwade, Basavaraj K. et al., "Functions of Lipids for Enhancement of Oral Bioavailability of Poorly Water-Soluble Drugs," *Sci Pharm.* (2011), 79:705-727.
Porter, Christopher H. et al., "Lipids and lipid-based formulations: optimizing the oral delivery of lipophilic drugs," *Nature Reviews/Drug Discovery* (Mar. 2007), 6:231-248.
Extract "Description and Solubility," *U.S. Pharmacopoeia* 30-NF25 (2007), 4 pages.
Cinnarizine: Definition; Characters: Identification; *Ph Eur monograph* 0816 printed Apr. 19, 2016 file:///C:/Users/GBrain/AppData/Local/Microsoft/Windows/Temporary%20Internet% . . . ; 4 pages.
Dumanli, Inayet, "Mechanistic Studies to Elucidate the Role of Lipid Vehicles on Solubility, Formulation and Bioavailability of Poorly Soluble Compounds," *Open Access Dissertations*, Paper 171, University of Rhode Island (2002); 246 pages.

(Continued)

*Primary Examiner* — Kortney L. Klinkel
*Assistant Examiner* — William Lee
(74) *Attorney, Agent, or Firm* — Mintz Levin Cohn Ferris Glovsky and Popeo, P.C.

(57) ABSTRACT

An oral pharmaceutical formulation containing an effective amount of NRC-AN-019 including its pharmaceutically acceptable salts and polymorphs such as Form I, Form II and Form III thereof to improve the bioavailability intended for self-emulsification upon its contact with the gastro-intestinal fluid. The invention also relates to a process for the preparation of oral solution containing NRC-AN-019 in an effective concentration for the better therapy against Chronic Myeloid Leukemia as BCR-ABL tyrosine kinase inhibitor and against other tumors such as head and neck cancer, prostate cancer and the like.

31 Claims, 1 Drawing Sheet

(56) References Cited

OTHER PUBLICATIONS

Griseofulvin: Accession No. DB00400 (APRD01004); http://www.drugbank.ca/drugs/DB00400; printed May 20, 2016; 12 pages.
Griseofulvin Monograph—*IARC Monographs* (2001); 79:291-315.
Halofantrine: Accession No. DB01218 (APRD011419); http://www.drugbank.ca/drugs/DB01218; printed May 20, 2016; 9 pages.
Kaukonen, Ann Marie et al., "Drug Solubilization Behavior During in Vitro Digestion of Simple Triglyceride Lipid Solution Formulations," *Pharmaceutical Research* (Feb. 2004); 21(2):245-253.
Larsen, Anne T. et al., "SNEDDS Containing Poorly Water Soluble Cinnarizine; Development and in Vitro Characterization of Dispersion, Digestion and Solubilization," *Pharmaceutics* (2012); 4:641-665.
Nielsen, Flemming S. et al., "Characterization of Prototype Self-Nanoemulsifying Formulations of Lipophilic Compounds," *Journal of Pharmaceutical Sciences*, (Apr. 2007); 96(4):876-892.
Pouton, Colin W. et al., "Formulation of lipid-based delivery systems for oral administration: Materials, methods and strategies," *Advanced Drug Delivery Reviews 60* (2008) 625-637 (Accepted Oct. 16, 2007).
Shahba, Ahmad Abdul-Wahhab Abdul-Majid, B.Sc. Pharm. (2005), "Influence of Self-Emulsifying Drug Delivery Systems on the Aqueous Solubility and Dispersion of Cinnarizine," (Thesis) Examined on Day Apr. 15, 1432 H-Mar. 20, 2011 D; 203 pages.
Sharif, Behzad et al., "Preparation and Evaluation of the Polymeric Micellar Formulation for Oral Delivery of Griseofulvin," *International Journal of Pharmacy* (Feb. 2014); 42(2):92-97.
Taillardat-Bertschinger, Agnes et al., "Partitioning of Halofantrine Hydrochloride between Water, Micellar Solutions, and Soybean Oil: Effects on its Apparent Ionization Constant," *Journal of Pharmaceutical Sciences* (Nov. 2003); 92(11):2217-2228.
Tokumura, Tadakazu et al., "Enhancement of the Oral Bioavailability of Cinnarizine in Oleic Acid in Beagle Dogs," *Journal of Pharmaceutical Sciences* (Apr. 1987); 76(4):286-288.

* cited by examiner

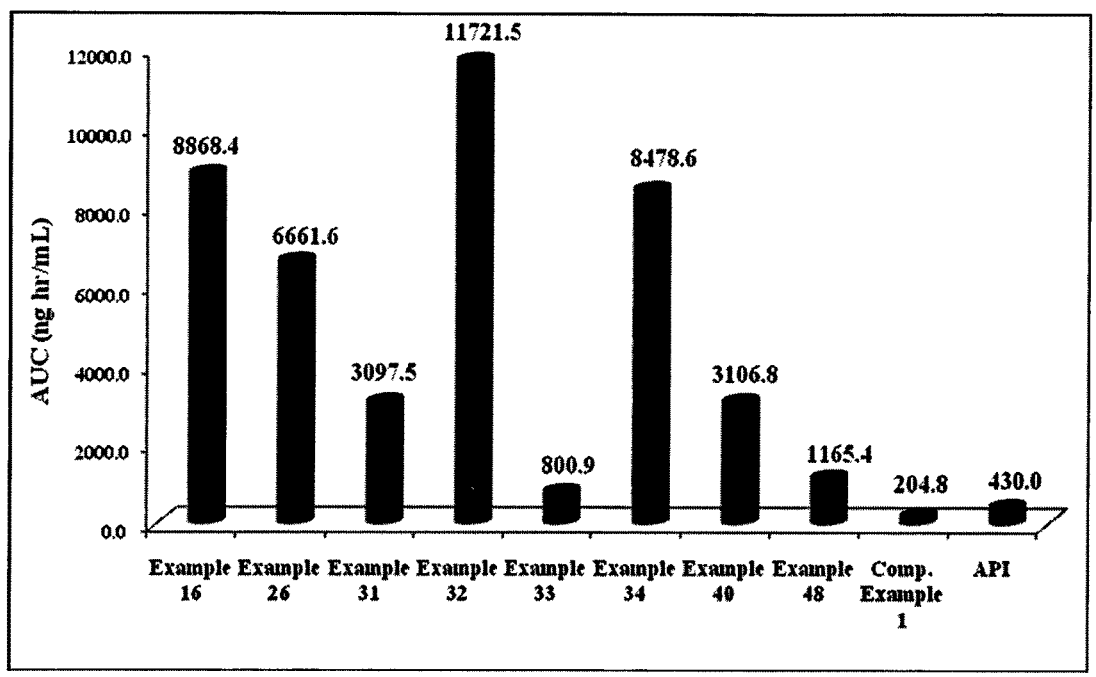
AUC (ng hr/mL) of NRC-AN-019 and its different formulations

FORMULATION COMPRISING PHENYLAMINOPYRIMIDINE DERIVATIVE AS ACTIVE AGENT

INTRODUCTION

The present invention pertains to the formulation of an oral solution intending for self-emulsification containing phenylaminopyrimidine derivative designated as development code NRC-AN-019 including its pharmaceutically acceptable salts and polymorphs such as Form I, Form II and Form III thereof for oral administration.

NRC-AN-019 is chemically known as (3,5-bis-trifluoromethyl)-N-[4-methyl-3-(4-pyridin-3-yl-pyrimidin-2-ylamino)-pheny-1]-benzamide, which is a phenylamino pyrimidine derivative and has been identified as a BCR-ABL tyrosine kinase inhibitor for the treatment of Chronic Myeloid Leukemia. NRC-AN-019 is also found to be an effective compound against other tumors such as head and neck cancer, prostate cancer and the like. Its structural formula is:

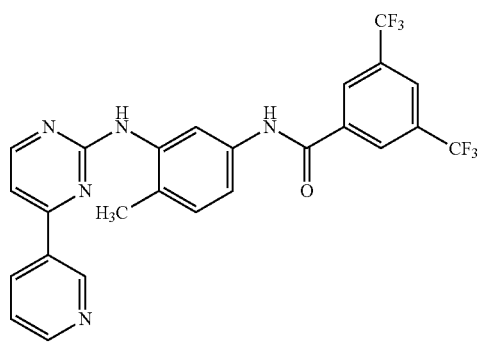 [SMILES: Cc1ccc(NC(=O)c2cc(C(F)(F)F)cc(C(F)(F)F)c2)cc1Nc1nccc(-c2cccnc2)n1]

NRC-AN-019 is a pale yellow to light brown coloured crystalline to amorphous powder. Its molecular formula is $C_{25}H_{17}F_6N_5O$ and its relative molecular mass is 517.44. NRC-AN-019 is practically insoluble in water, very slightly soluble in aqueous buffer of pH 1.2 and is insoluble in neutral/alkaline aqueous buffers. The drug substance is soluble in dimethyl formamide and dimethyl sulfoxide.

The present invention relates to an oral dosage form containing a therapeutically effective amount of NRC-AN-019 including its pharmaceutically acceptable salts and polymorphs such as Form I, Form II and Form III thereof. The present invention particularly relates to a self-emulsifying drug delivery formulation containing NRC-AN-019 in solution suitable for oral administration. The formulation of the present invention is useful as an antineoplastic agent for treatment of Chronic Myeloid Leukemia and some other tumors such as head and neck cancer, prostate cancer and the like. The invention also relates to a process for the preparation of the said formulation.

BACKGROUND AND PRIOR ART OF THE INVENTION

NRC-AN-019 is a protein-tyrosine kinase inhibitor; it inhibits the abnormal function of BCR-ABL tyrosine kinase, which is produced by the Philadelphia chromosome abnormality and is found in Chronic Myeloid Leukemia (CML). NRC-AN-019 inhibits cell proliferation and induces apoptosis (programmed cell death) in the BCR-ABL cell lines and in the leukemic cells generated by CML. It also acts effectively against other tumors such as head and neck cancer, prostate cancer and the like.

Since the initial discovery of tyrosine-specific protein kinases encoded by the transforming viruses and their normal cellular homologues, there has been a great deal of interest in understanding their role in cancer and exploring their potential as therapeutic targets. BCR-ABL tyrosine kinase inhibitors started an era of molecular targeted therapy and marked a great milestone in cancer drug discovery.

Oral drug administration is the most generally accepted route of administration for treating diseases. The lipophilic drugs exhibit poorer solubility and release rate when administered as conventional tablets or capsules and thus exhibit lower bioavailability. Therefore, in solving the problem of low bioavailability of a poorly soluble drug, improvement of the absorption of the orally administered drug is the key point.

Considering the drug bioavailability and variability in patient dose response, NRC-AN-019 presents specific difficulties in relation to solubility and its formulation development. The inventors of this present application have surprisingly found that lipid-based formulation technology provides a therapeutically effective platform for the delivery of NRC-AN-019 in terms of bioavailability and pharmacological response.

Novel phenylaminopyrimidine derivatives have been disclosed as inhibitors of BCR-ABL kinase for the therapy of Chronic Myeloid Leukemia in U.S. Patent application no. 20070232633 corresponding PCT application no. PCT/IN05/000243. The novel intermediates which are useful for the preparation of novel phenylaminopyrimidine derivatives have also been disclosed in the aforementioned patent application.

The above U.S. patent application particularly describes novel phenylaminopyrimidine derivatives of the general formula I, which can be used in the therapy of Chronic Myeloid Leukemia (CML) with pharmaceutically acceptable carriers that are suitable for topical, enteral, for example oral or rectal, or parental administration, and may be inorganic or organic, solid or liquid. In addition to the active ingredient(s), the pharmaceutical compositions of the mentioned invention may contain one or more excipients or adjuvants.

Example 14 of the said PCT application no. PCT/IN05/000243 discloses capsule formulations, comprising active compounds which are prepared by the process described in Example-1: (3-trifluoromethyl)-N-[4-methyl-3-(4-pyridin-3-yl-pyrimidin-2-yl-amino)-phenyl]-benzamide and Example-3: (3,5-bis trifluoromethyl)-N-[4-methyl-3-(4-pyridin-3-yl-pyrimidin-2-ylamino)-pheny-1]-benzamide, including lactose, polyvinylpyrrolidone, crospovidone and magnesium stearate as excipients.

A particular form of (3,5-bis trifluoromethyl)-N-[4-methyl-3-(4-pyridin-3yl-pyrimidin-2ylamino)-phenyl]-benzamide has been disclosed in U.S. Patent application no. 20080306100 corresponding PCT application no. PCT/IN05/000243 and the compound has been designated as AN-019. It also discloses the process for the preparation thereof and the pharmaceutical compositions containing this crystal form with their use as anti tumor agents in humans.

The disclosure of the different polymorphs Form I, Form II and Form III is highlighted by U.S. Patent application no. 20090227611 corresponding PCT application no. PCT/IB09/005421. It is disclosed that, inspite of the exhibition of valuable pharmacological properties as anti tumor activities by all the aforementioned forms, Form III was found to have better thermodynamic stability. As used herein, references to the Form I, Form II and Form III polymorphs are to the corresponding polymorphs described in PCT/IB09/005421, the disclosure of which is incorporated herein by reference.

It is very well known that phenylaminopyrimidine derivatives are found to be very useful for the treatment of BCR-ABL positive cancer and tumor diseases, such as leukemias [especially Chronic Myeloid Leukemia (CML) and Acute Lymphoblastic Leukemia, where especially apoptotic mechanisms of action are found]. Consequently, interest and attention are being given for developing more new molecules followed by formulations for the effective therapy.

As (3,5-bis-trifluoromethyl)-N-[4-methyl-3-(4-pyridin-3-yl-pyrimidin-2-ylamino)-pheny-1]-benzamide, which is a novel phenylaminopyrimidine derivative designated as NRC-AN-019, has been mentioned in the prior art and which has been identified as BCR-ABL tyrosine kinase inhibitor for the treatment of Chronic Myeloid Leukemia, the need arises for developing a suitable dosage form for oral administration for warm-blooded animals such as humans.

The use of the NRC-AN-019 as an active pharmaceutical ingredient in the formulation of the present invention has not been described in any of the prior art.

The capsule formulation disclosed in an embodiment of the U.S. Patent application no. 20070232633 corresponding PCT application no. PCT/IN05/000243 was found to have very poor absorption characteristics; hence the need arises to develop better dosage forms capable of giving good bioavailability and optimum therapeutic levels in the blood to elicit the drug action.

Development of this novel phenylaminopyrimidine derivative has been contemplated by our scientists to develop an orally administrable dosage form for better patient compliance.

For the reasons cited above, a need arose to develop an orally administrable formulation for increasing the bioavailability of this novel phenylaminopyrimidine derivative.

In an aspect, the present invention specifically provides formulations comprising NRC-AN-019 as an active ingredient, which compositions are in the form of a solution. The formulation of the present invention embodied herein provides a system capable of spontaneously forming an emulsion upon contact with the gastric fluid.

There is a need to work on formulations and process thereof, which proves better therapeutic efficacy, ease of oral administration and to be economical for large-scale production.

OBJECTIVES OF THE INVENTION

Accordingly, the main objective of the present invention is to design and develop an orally administrable pharmaceutical composition of NRC-AN-019, including its pharmaceutically acceptable salts and polymorphs such as Form I, Form II and Form III thereof which are BCR-ABL tyrosine kinase inhibitors and thus can be effectively used against Chronic Myeloid Leukemia (CML) and some other tumors such as head and neck cancer, prostate cancer and the like.

Another objective of this invention is to provide orally administrable pharmaceutical composition in the form of an oral solution, since NRC-AN-019 presents specific difficulties in relation to its oral administration, with regard to its solubility, bioavailability and variability in patient dose response.

Accordingly, a further objective of this invention is to provide the pharmaceutical composition of an oral solution in the form of a lipid based formulation and to achieve better therapeutic levels for the therapy against aforementioned diseases.

More especially, the present invention aims to develop a process for preparing the oral solution comprising NRC-AN-019, a lipid phase, surfactant(s) and a water miscible solvent.

Still another objective of the present invention is to provide a method for enhancing the bioavailability of a lipophilic drug in a patient undergoing therapy, comprising oral administration to the said patient with the pharmaceutical composition of the present invention.

Yet another objective of the present invention is the self emulsification of the formulation upon oral administration after coming in contact with the gastric fluid followed by increase in the bioavailability of the pharmaceutical ingredient.

Yet another objective of the present invention is bringing the lipophilic phase, the surfactant(s) and solvent phase, into intimate admixture and adding the active agent to form the solution.

Yet another objective of the present invention solution is to optionally fill the formulation of the present invention into capsules or to be adsorbed onto the surface of any adsorbing material, followed by formulation into discrete dosage forms either as tablets or capsules.

STATEMENT OF INVENTION

Accordingly, the present invention provides a pharmaceutical oral formulation containing NRC-AN-019 including its pharmaceutically acceptable salts and its polymorphs such as Form I, Form II and Form III thereof and a process for its preparation to enhance the bioavailability so as to achieve effective therapy against Chronic Myeloid Leukemia and other tumors such as head and neck cancer, prostate cancer and the like.

The present invention also provides a method of treating cancer which method comprises administering to a patient in need thereof the pharmaceutical composition of the present invention.

The present invention also provides a pharmaceutical composition for use in the treatment of the human or animal body.

The present invention also provides the use of the formulation of the present invention in the manufacture of a medicament for the treatment of cancer.

DETAILED DESCRIPTION OF THE INVENTION

The present invention provides a pharmaceutical composition in the form of self emulsifying system which is capable of forming an in-situ emulsion after oral administration when it comes in contact with the gastric fluid, comprising NRC-AN-019 as an active ingredient useful for the treatment of CML and other tumors such as head and neck cancer, prostate cancer and the like.

The present invention provides a pharmaceutical composition for oral administration comprising:
 (a) a therapeutically effective amount of (3,5-bis trifluoromethyl)-N-[4-methyl-3-(4-pyridin-3yl-pyrimidin-2yl amino)phenyl]benzamide (NRC-AN-019) or a pharmaceutically acceptable salt thereof;

(b) a lipophilic phase;
(c) at least one pharmaceutically acceptable surfactant; and
(d) a pharmaceutically acceptable water miscible solvent.

The present invention applies to the formulation development of NRC-AN-019, chemically known as (3,5-bis-trifluoromethyl)-N-[4-methyl-3-(4-pyridin-3-yl-pyrimidin-2-ylamino)-pheny-1]-benzamide which is having therapeutic utility, e.g. as a tyrosine kinase inhibitor for treatment of Chronic Myeloid Leukemia, head and neck cancer and prostate cancer and is found to exhibit useful anti-tumor activity. NRC-AN-019 targets BCR-ABL (a protein-tyrosine kinase) which is the important target for the treatment of Chronic Myeloid Leukemia. The specific inhibitors of BCR-ABL kinase e.g. compound are attractive therapeutic agents as these kinases regulate many cellular processes, including growth and survival, and deregulated activity of these enzymes has been implicated in malignant transformation in various neoplasms. The development of this compound represents a monumental research effort that is beginning to show good clinical promise.

NRC-AN-019 is highly hydrophobic thus the bioavailability levels achieved with other oral dosage forms such as capsules, tablets are low and exhibit wide variation in therapeutic levels. To achieve effective anti-malignant therapy, the blood serum level of the active compound has to be maintained within a specified range and ensure optimum therapeutic window.

An overriding difficulty which accounts for the less bioavailability problem is the inherent insolubility of the NRC-AN-019 e.g. in aqueous media and hence provision of a dosage form which can contain drug in sufficiently effective concentration to permit convenient use and yet meet the required criteria in terms of bioavailability e.g. enabling effective absorption from the stomach or gut lumen and achievement of consistent and appropriately effective blood serum levels.

The primary mechanisms by which lipid based formulations enhance bioavailability is through solubilization of the drug and include reduction of p-glycoprotein mediated efflux, mitigation of hepatic first pass metabolism through enhanced lymphatic transport, prolongation of gastrointestinal transit time or, protection from degradation in the gastro intestinal tract. This helps in rapid and less variable absorption.

Typically, in the formulation of the present invention, NRC-AN-019, including the pharmaceutically acceptable salts and polymorphs such as Form I, Form II and Form III thereof, is used in an amount of about 0.05% by weight to about 50% by weight, preferably about 0.1% by weight to about 20% by weight and more preferably about 0.25% by weight to about 10% by weight, based on the total weight of the composition.

The lipophilic phase in the composition of the invention typically comprises a pharmaceutically acceptable lipophilic medium, such as a triglyceride, a diglyceride, a monoglyceride, a fatty acid or a derivative of a fatty acid, or a mixture thereof. Typically, the fatty acids have a carboxyl moiety attached to a linear or branched, saturated or unsaturated $C_1$ to $C_{21}$ aliphatic moiety. Long chain fatty acids, including $C_{12}$ to $C_{22}$ fatty acids wherein said aliphatic moiety contains 11 to 21 carbon atoms; medium chain fatty acids, including $C_6$ to $C_{11}$ fatty acids wherein said aliphatic moiety contains 5 to 10 carbon atoms; and short chain fatty acids, including $C_2$ to $C_5$ fatty acids wherein said aliphatic moiety contains 1 to 4 carbon atoms, are suitable, with long and medium chain fatty acids or triglycerides thereof being particularly preferred.

Examples of fatty acids which can be present in the lipophilic phase in free acid form or as triglyceride, diglyceride or monoglyceride esters, include acetic acid, propionic acid, butyric acid, valeric acid, caproic acid, enanthic acid, caprylic acid, pelargonic acid, capric acid, undecylic acid, lauric acid, tridecylic acid, myristic acid, pentadecylic acid, palmitic acid, margaric acid, stearic acid, nonadecylic acid, arachidic acid, heneicosylic acid, behenic acid, α-linolenic acid, stearidonic acid, eicosapentaenoic acid, docosahexaenoic acid, linoleic acid, γ-linolenic acid, lihomo-γ-linolenic acid, arachidonic acid, oleic acid, elaidic acid, eicosenoic acid, erucic acid, nervonic acid and ricinoleic acid.

More typically, the lipophilic phase comprises mixtures of mono-, di- and triglycerides, which mono-, di- and triglycerides contain $C_{12}$ to $C_{20}$ fatty acid residues attached to at least one alcohol group on the glyceride moiety. Preferably, said $C_{12}$ to $C_{20}$ fatty acid residues are attached to each alcohol group in the glyceride moiety. Preferably, said $C_{12}$ to $C_{22}$ fatty acid residues are $C_{16-18}$ fatty acid residues. Said mixed mono-, di- and triglycerides may carry both saturated and unsaturated fatty acid residues.

In a preferred embodiment, the lipophilic phase in the formulation of the present invention comprises unsaturated fatty acid residues, typically $C_{18}$ unsaturated fatty acid residues such as ricinoleic acid, linolenic acid, linoleic acid and oleic acid. Typically, the said unsaturated fatty acid residues are present in an amount of at least 20% by weight, more preferably at least 40% by weight or more based on the total weight of the lipophilic phase. Preferably, saturated fatty acids residues, such as stearic acid, myristic acid and palmitic acid residues are present in an amount of 50% by weight or less based on the total weight of the lipophilic phase.

The lipophilic phase in the pharmaceutical composition of the present invention may be obtained by the hydrolysis of various animal and vegetable fats and oils, e.g., olive oil followed by the separation of the liquid acids. A preferred liquid acid obtainable in this way is (Z)-9-octadecenoic acid, also known as oleic acid. Oleic acid is a monounsaturated omega-9 fatty acid (meaning that the only carbon-carbon double bond occurs at the ninth carbon atom from the free end of the aliphatic moiety), found in various animal and vegetable sources. Oleic acid can be characterized by specific gravity of 0.889-0.895, an acid value of 196-204, an iodine value of 85-95, a density of 0.895 g/cm$^3$ and a melting point of 4° C.

Typically, the lipophilic phase of the pharmaceutical composition of the present invention is present in an amount of about 5% by weight to about 85% by weight, preferably about 10% by weight to about 75% by weight and more preferably about 12.5% by weight to about 65% by weight based on the total weight of the composition.

In a preferred embodiment, the lipophilic phase of the formulation of the present invention comprises an ester of an alcohol with $C_{8-10}$ fatty acids, such as mono-, di- and mono/di-glycerides of medium chain fatty acids e.g. caprylic and capric acids and mixtures thereof, neutral oils such as neutral plant oils, in particular fractionated coconut oils which are known commercially under the trade name Miglyol, available as Miglyol 810 and Miglyol 812 (fractionated coconut oil comprising caprylic-capric acid triglycerides) and Miglyol 818 (caprylic-capric-linoleic acid triglyceride), Captex 355 (caprylic-capric acid triglycerides) and the like. Other suitable caprylic-capric acid triglycerides known and commercially available as under the trade name Myritol including the product Myritol 318. Further suitable products of this class are Captex 300 (Triglycerides of caprylic/capric acid) and Captex 800 (Propylene glycol diethylhexanoate), Neobee M 5 (caprylic/capric triglyceride) and the like.

In a further preferred embodiment, the lipophilic phase of the formulation of the present invention comprises a pharmaceutically acceptable oil, preferably with an unsaturated component such as a vegetable oil or fish oil. The lipophilic phase may also comprise suitable transesterified ethoxylated vegetable oils such as those obtained by reacting various natural vegetable oils (for example, maize oil, kernel oil, almond oil, ground nut oil, olive oil, soyabean oil, sunflower oil, corn oil, safflower oil and palm oil, or mixture thereof) with polyethylene glycols that have a molecular weight of from 200-800, in the presence of an appropriate catalyst. Transesterified ethoxylated vegetable oils are known and are commercially available under the trade name Labrafil (for example Labrafil M 2125CS, Labrafil M 1944 CS, Labrafil M 2130 CS) and the like.

The formulation of the present invention also comprises one or more pharmaceutically acceptable surfactants. Surfactants facilitate the hydrophilic lipophilic balance (HLB) value required for emulsification. The surfactant component may comprise hydrophilic or lipophilic surfactants or mixture thereof. As used herein, a hydrophilic surfactant has an HLB value greater than 10 and a lipophilic surfactant has an HLB value less than 10. Especially preferred are nonionic hydrophilic and nonionic lipophilic surfactants.

Typically, said hydrophilic surfactant is a surfactant with a relatively high HLB value, typically 11 to 15, more typically 12 to 14, comprising but not restricted to reaction products of natural or hydrogenated vegetable oils and ethylene glycol, which reaction products are polyoxyethylene glycolated natural or hydrogenated vegetable oils, e.g. polyoxyethylene glycolated natural or hydrogenated castor oils. Such products may also be obtained by reaction of a natural or hydrogenated castor oil with ethylene oxide, e.g. in a molar ratio of 1:5 to about 1:200 followed with an optional purification process. The product Cremophor EL is especially preferred and can be prepared by reacting 1 mole of castor oil with 35-40 moles of ethylene oxide and is chemically known as polyoxyl-35-castor oil.

Cremophor EL has a saponification value of 65-70, an acid value≤2.0, an iodine value 25-35, HLB value 12-14, hydroxyl value of 65-78, water content (%) of 2.8 (Fisher value) and melting point of 19-20° C.

Other hydrophilic surfactants suitable for use in the present invention include tensides, such as that available under the trade name Nikkol HCO-60 which is a reaction product of hydrogenated castor oil and ethylene oxide.

Further examples of said hydrophilic surfactant include polyoxyethylated sorbitan fatty acid esters e.g. polyoxyethylene derivatives of mono- and tri-lauryl, palmtyl, stearyl or oleyl esters of sorbitan, such as those known and commercially available under the trade name Tween including the products: Tween 20 [polyoxyethylene (20) sorbitan monolaurate], Tween 21 [polyoxyethylene (4) sorbitan monolaurate], Tween 40 [polyoxyethylene (20) sorbitan monopalmitate], Tween 60 [polyoxyethylene (20) sorbitan monostearate], Tween 61 [polyoxyethylene (4) sorbitan monostearate], Tween 65 [polyoxyethylene (20) sorbitan tristearate], Tween 80 [polyoxyethylene (20) sorbitan monooleate], Tween 81 [polyoxyethylene (5) sorbitan monooleate], Tween 85 [polyoxyethylene (20) sorbitan trioleate], Tween 120 [polyoxyethylene (20) sorbitan monoisostearate]. Preferably, the polyoxyethylene sorbitan fatty acid ester used in the compositions of the invention is Tween 80 [polyoxyethylene (20) sorbitan monooleate], which has a hydroxyl value of 65-80, acid value of 2% and saponification value of 45-55.

Other hydrophilic surfactants that can be used are polyoxyethylene fatty acid esters, polyoxylglycerides, polyoxyethylene-polyoxypropylene co-polymers, dioctylsuccinate, dioctylsodiumsulfosuccinate or sodium lauryl sulphate, phospholipids (in particular lecithin), propylene glycol mono- and di-fatty acid esters, bile salts and the like.

The amount of hydrophilic surfactant used is typically in the range of about 5% by weight to about 60% by weight, preferably about 10% by weight to about 50% by weight based on the total weight of the composition.

Typically, in another embodiment of the present invention, the lipophilic surfactant is a surfactant with a relatively low HLB value, typically 5 to 7, more typically 4 to 8, such as, but not restricted to sorbitan fatty acid esters e.g. of the type known and commercially available under the trade name Span, for example including sorbitan-monolauryl, -monopalmityl, -monostearyl, -tristearyl, -monooleyl and trioleyl esters.

Other examples of lipophilic surfactants which may be used in the present invention include trans-esterification products of natural vegetable oil triglycerides and polyalkylene polyols, mono-, di- and mono/di glycerides (especially esterification products of caprylic or capric acid with glycerol), sorbitan fatty acid esters, pentaerythriol fatty acid esters and polyalkylene glycol ethers, monoglycerides, glycerol triacetate or triacetin, sterols, derivatives thereof, and the like.

The amount of lipophilic surfactant used is typically in the range of about 5% by weight to about 60% by weight, preferably about 10% by weight to about 50% by weight of the total weight of the composition.

Typically, said at least one pharmaceutically acceptable surfactant is at least one said lipophilic surfactant. In another embodiment said at least one pharmaceutically acceptable surfactant is at least one hydrophilic surfactant. In another embodiment said at least one pharmaceutically acceptable surfactant is at least one surfactant selected from hydrophilic and lipophilic surfactants. In another embodiment, the said at least one pharmaceutically acceptable surfactant is at least one surfactant from hydrophilic or lipophilic surfactants.

In one embodiment, the formulation of the present invention comprises at least one from the abovementioned surfactants.

Typically, the pharmaceutical composition of the present invention comprises a lipophilic or hydrophilic surfactant, as defined above, as a principal surfactant and one or more co-surfactants. When a co-surfactant is present it may be selected from any of the surfactant types indicated in the aforementioned surfactant categories. The co-surfactant phase adds potentiation effect to the effectiveness of the principal surfactant.

Preferably, the co-surfactant is a polyoxylglyceride, which is obtainable by (i) the partial alcoholysis of vegetable oils using macrogols, (ii) by esterification of glycerol and macrogols with unsaturated fatty acids, and (iii) by mixing glycerol esters and condensates of ethylene oxide with fatty acids of vegetable oils. Typically, the polyoxylglycerides used as co-surfactants include mixtures of monoesters, diesters, and triesters of glycerol, and monoesters and diesters of polyethylene glycols (PEG), preferably having a mean relative molecular mass between 200-400. Such polyoxylglycerides are obtainable as the product of partial alcoholysis of medium chain triglycerides with polyethylene glycol, caprylic (octanoic) acid and capric (decanoic) acid or obtainable by mixing glycerine esters and condensates of ethylene oxide with caprylic acid and capric acid.

The preferred polyoxylglyceride co-surfactants for use in the present invention are caprylocaproyl polyoxylglycerides such as those commercially available under trade name Labrasol, which has an acid value of ≤2.0, iodine value of ≤2.0, saponification value of 85-105 and a hydroxyl value of 170-205.

Optionally the other co-surfactants that can be used are Lauroyl polyoxylglycerides commercially available under trade name Gelucire 44/14, Linoleoyl polyoxylglycerides commercially available under trade name Labrafil M2125CS, Oleoyl polyoxylglycerides commercially available under trade name Labrafil M1944CS, Stearoyl polyoxyl glycerides commercially available under trade name Gelucire 50/13.

When a co-surfactant is present, it is typically used in the range of about 2% by weight to about 60% by weight, and preferably about 5% by weight to about 45% by weight of the total weight of the composition.

In one particularly preferred embodiment, the said principal surfactant is polyoxyl 35 castor oil and the said one or more co-surfactant is caprylocaproyl polyoxyl 8 glyceride.

In another particularly preferred embodiment, the said principal surfactant is polyoxyl 35 castor oil and the said one or more co-surfactants are caprylocaproyl polyoxyl 8 glyceride and polysorbate 80.

In yet another particularly preferred embodiment, the said principal surfactant is polyoxyl 35 castor oil and the said one or more co-surfactant is glycerol monocaprylocaprate.

In another still particularly preferred embodiment, the said principal surfactant is polyoxyl 35 castor oil and the said one or more co-surfactant is ethyl oleate.

The total amount of the surfactant phase used is typically in the range of about 4% by weight to about 70% by weight and preferably about 8% by weight to about 60% by weight of the total weight of the composition.

The formulation of the present invention further comprises a pharmaceutically acceptable water miscible solvent. The water-miscible solvent used in the present invention serves as a carrier medium for NRC-AN-019, assisting in solubilization of high concentration of the drug as well as facilitating ingress of water into the formulation. In accordance with the present invention, an especially preferred solvent comprises of pharmaceutically acceptable water miscible solvent is an α-hydro-ω-hydroxypoly(oxy-1,2-ethanediyl) derivative which has an average molecular weight of 570-613, a flash point of 250° C., density of 1.080 g/cm$^3$, a hydroxyl value of 178-197 and a viscosity of 9.9-11.3 mm$^2$/s (at 98.9° C.±0.3° C.). Particularly preferred is a polyethylene glycol having an average molecular weight of 600, known commercially as POGOL 600. Other examples include a diethylene glycol monoethyl ether having an average molecular weight of from 134.2; a density of 0.988 g/cm$^3$; a hydroxyl value of 300-400 and a boiling point of from 197-205° C.

The use of components defined as above has in particular been found to provide compositions in which the water miscible solvent is especially suitable as an NRC-AN-019 carrier medium.

The compositions in accordance with the formulation comprising components as mentioned as water miscible solvent may of course include additionally or alternatively one or more other ingredients as solvent phase.

Further examples of suitable water miscible solvents include polyoxyethylene, propylene carbonate, tetrahydrofurfuryl alcohol, polyethylene glycol ether, glycerol, propylene glycol, polyethylene glycols and lower alkanols in particular $C_1$ to $C_8$ alkanols such as ethanol and benzyl alcohol. Though the use of alkanols e.g. ethanol and/or benzyl alcohol as the solvent phase components is contemplated by the inventors of the present invention for reasons, this will be generally less preferred.

Said pharmaceutically acceptable water miscible solvent may of course comprise a mixture of two or more different solvents. NRC-AN-019 will, however, typically have sufficient solubility in any solvent present such a mixture such that the efficacy of the carrier system is not materially impaired.

The amount of water miscible solvent present is typically about 2% by weight to about 60% by weight, preferably about 5% by weight to about 30% by weight and more preferably about 5.5% by weight to about 25% by weight based on the total weight of the composition.

The formulation of the invention may optionally comprise one or more antioxidants in a suitable concentration range to prevent oxidative rancidity of the lipid phase used in the said composition. Suitable antioxidants include α-tocopherol, ascorbic acid palmitate, butylated hydroxyanisole (BHA), butylated hydroxytoluene (BHT), alkyl gallates like propyl gallate, lauryl gallate, or octyl gallate, carotenes, carnosic acid and the like.

Preferably, the antioxidant is a free radical-scavenging antioxidant. More preferably the antioxidant is selected from butylated hydroxytoluene, butylated hydroxyanisole and a mixture thereof. One or more antioxidants, if desired, are present in compositions of the invention in a certain ratio with respect to the stability aspects of the pharmaceutical composition.

Butyl hydroxy anisole and butyl hydroxy toluene may be employed as antioxidants either individually or in combination. When used in combination, they are preferably used in a ratio of from 6:4 to 9:1, more preferably in a ratio of from 7:3 to 8:2.

The butyl hydroxy anisole antioxidant is typically used in the range of about 0.01% by weight to about 5% by weight, preferably about 0.02% by weight to about 3% by weight and more preferably about 0.05% by weight to about 2% by weight based on the total weight of the composition. The amount of butyl hydroxy toluene used is typically in the range of about 0.001% by weight to about 4% by weight, preferably about 0.002% by weight to about 3% by weight and more preferably about 0.01% by weight to about 0.5% by weight based on the total weight of the composition.

Compositions of the present invention optionally comprise one or more nutraceutically acceptable oil soluble sweetening agents. The sweetening agent may be used for better patient acceptability of the dosage form. Typically the sweetening agent is selected from mannitol, sodium saccharine, propylene glycol, acesulfame K, sucralose, neotame, aspartame and saccharin. The sweetener may also enhance the flavor system.

The amount of sweetening agent used is typically in the range of about 0.1% by weight to about 10% by weight, and preferably about 0.25% by weight to about 5% by weight based on the total weight of the composition.

Compositions of the present invention optionally comprise one or more nutraceutically acceptable flavoring agents. Flavoring agents can enhance patient compliance by making the composition more palatable.

Flavoring agents, which are oil soluble are known to those skilled in the art and include spearmint oil, de-mentholised peppermint oil, lemon oil, cinnamon leaf oil, cinnamon bark oil, cardamom oil, caraway oil, coriander seed oil, thyme oil, cinnamon oil, orange oil, star anise oil, dill seed oil, fennel oil, nutmeg oil benzaldehyde, cinnamaldehyde, sodium formaldehyde sulfoxylate, vanillin, ethyl vanillin and ethyl acetate. Such flavoring agents give rise to clear and homogeneous formulations which are aesthetically appealing to the consumer.

The amount of flavoring agent used is typically in the range of about 0.1% by weight to about 10% by weight and preferably about 0.25% by weight to about 5% by weight based on the total weight of the composition.

Compositions of the present invention optionally comprise one or more coloring agents. Coloring agents may be added to provide a product with a more aesthetic and/or distinctive appearance. Suitable coloring agents include oleoresin turmeric, oleoresin paprika, oleoresin marigold and the like.

The coloring agents can be used in the range of about 0.025% by weight to about 0.25% by weight, preferably about 0.05% by weight to about 0.2% by weight and more preferably about 0.01% by weight to about 0.1% by weight of the total weight of the composition.

Compositions of the present invention optionally comprise one or more nutraceutically acceptable preservatives. Non-limiting examples of such preservatives include benzoic acid, sodium benzoate, benzethonium chloride, benzyl alcohol, chlorobutanol, phenylethyl alcohol, methylparaben, propylparaben etc.

Compositions of the present invention optionally comprise stabilizers like acidifiers which may be lipid soluble and/or ethanol soluble. The acidifier may be for example a fatty acid or, a carboxylic acid, typically a mono-, di- or tri-carboxylic acid, preferably a mono- or dicarboxylic acid. The acidifier may comprise one or more hydrophilic groups, e.g. hydroxy groups, preferably one or two hydrophilic groups. Suitable acids for use in this invention include oleic acid, malonic acid, fumaric acid, famonic acid, maleic acid, D-malic acid, L-malic acid, citric acid, succinic acid, oxalic acid, benzoic acid or lactic acid or an acid with a similar pKa, e.g. 2-7. Preferred acidifiers include malonic acid, oxalic acid, citric acid and lactic acid to increase the stability during the storage and utilization period.

Compositions of the present invention optionally comprise one or more thickening agents. Suitable thickening agents include those known and employed in the art, including, e.g. pharmaceutically acceptable polymeric materials. Examples of thickening agents include polyacrylate and polyacrylate copolymer resins, polyvinyl pyrolidone, polyvinyl resins, inorganic thickening agents and the like, celluloses and derivatives thereof for example methyl-, ethyl- and propyl celluloses; hydroxyalkyl-celluloses, e.g. hydroxyl propyl celluloses and hydroxylpropylalkyl celluloses and the like including salts thereof preferably hydroxy propyl methyl cellulose. The thickening agent may act as a precipitation inhibitor so that if super saturation is achieved, then it can be extended for prolonged period of time which may add additional effective features to the therapeutic window.

Compositions in accordance to the specific embodiments of this application disclose the proportions of each component which upon being added to the water or gastric fluid of a specific volume intends to provide a self emulsifying drug delivery system.

This formulation of the present invention is intended for self-emulsification in-vivo when it comes into contact with the gastric fluids and thus followed by the enhanced absorption rate and increased bioavailability. It may be in the form of a solution, a soft gel or a hard shell capsular formulation.

Compositions in accordance with the present invention may be employed for administration in any appropriate manner, e.g. orally along with water, fruit juices and/or milk which are described elsewhere in the application. The other suitable orally administrable dosage forms include discrete dosage forms for example a soft gel and hard shell capsular formulations.

Suitable encapsulation material, for example, the gelatin or HPMC capsules, may be used. Therefore, another embodiment of the present invention is a concentrated composition, either a solution or solution/suspension, wherein the composition is formulated as a discrete dose unit or units, for example a soft gel and hard shell capsular formulations. Suitable encapsulation material, for example, the gelatin or HPMC capsules, may be used. The liquid-filling & band-sealing technology, Liquid Encapsulation by MicroSpray technique or Quali-Seal technique can be used for the encapsulation into hard gelatin capsules.

The resulting solution obtained can be optionally directly filled into the hard gelatin capsules or soft gelatin capsule or else can also be adsorbed onto the surface of any adsorbing material, followed by compression into compacted mass or encapsulation.

Concentrated solutions or solutions can be encapsulated by any method known in the art including the plate process, vacuum process, or the rotary die process. By the rotary die process, liquid encapsulation material, for example gelatin, flowing from an overhead tank is formed into two continuous ribbons by a rotary die machine and brought together by twin rotating dies. Simultaneously, metered fill material is injected between ribbons at the same moment that the dies form pockets of the ribbons. These pockets of fill-containing encapsulation material are then sealed by pressure and heat, and the capsules are served from the machine. Soft gel capsules may be manufactured in different shapes including round, oval, oblong, and tube-shape, among others. Additionally, by using two different ribbon colors, two-tone capsules can be produced.

The toxicological study of NRC-AN-019 shows the maximum tolerated oral dose in rats is >5000 mg/kg bodyweight and that of the formulation of the present invention shows 60 mg/kg bodyweight in Beagle dogs.

The MTT (3-[4,5-dimethylthiazol-2-yl]-2,5-diphenyltetrazolium bromide) assay was carried out to compare the activity of NRC-AN-019 active pharmaceutical ingredient against the formulation of the present invention on CAL-27 (Tongue squamous cell carcinoma) cell line at $1.75 \times 10^4$ cells/mL using dilutions of 10 µM to and 0.0156 µM/mL for 72 hours. The $IC_{50}$ values for NRC-AN-019 as active pharmaceutical ingredient and in formulation of the present invention are 1441 nM and 864 nM respectively, thereby showing substantially better activity of the formulation of the present invention.

The further study of MTT Assay on PC3M (Prostate Cancer) Cell lines to compare the activity of NRC-AN-019 active pharmaceutical ingredient against formulation of the present invention at $0.312 \times 10^5$ cells/mL for 72 hours described that the IC/50 values for NRC-AN-019 as active pharmaceutical ingredient and in formulation of the present invention are 4381 nM and 938 nM respectively which revealed nearly four-fold greater activity of the formulation.

The formulation of the present invention is found to be stable throughout the stability testing storage period.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope. The invention has been described with reference to various specific and preferred embodiments and techniques. However, it should be understood that many variations and modifications may be made while remaining within the rationale and scope of the invention.

FIG. 1 shows the bioavailability study of the formulation of the present invention with respect to the capsule dosage forms disclosed in earlier patents and the active pharmaceutical ingredient. The study discloses the better bioavailability characteristics of NRC-AN-019 in the formulation of the present invention than in the other forms like active pharmaceutical ingredient and the capsule dosage form, thus the optimum bioavailability can be achieved for the therapeutic effectiveness of NRC-AN-019. The data suggests that the time required for achieving the maximum concentration of the drug is less for the formulation of the present invention than that of the active pharmaceutical ingredient and the maximum concentration and AUC of the formulation of the present invention are substantially higher than that of the capsule formulation and Active Pharmaceutical Ingredient.

The details of the process of the invention are provided in the examples given below which is provided by way of illustration only and therefore should not be construed to limit the scope of the invention. The preparation of the present invention that can be administered by the oral route is carried out according to the following process:

EXAMPLES

The components illustrated in Examples 1 to 52 and Comparative Example 1 are expressed in % by weight based on the total weight of each composition.

In a specific embodiment the present invention provides a process for preparation of a composition, which comprises intimately mixing NRC-AN-019 with solvent phase, followed by the addition of lipophilic phase, co-surfactant and surfactant phase under stirring with the application of heat for the intimate mixing until a clear solution is obtained or as mentioned under individual examples.

The compositions of Example 1 to 34, contains the fatty acid as the lipophilic phase

TABLE 1

| Components | Example 1 % (w/w) | Example 2 % (w/w) | Example 3 % (w/w) |
|---|---|---|---|
| NRC-AN-019 | 0.99 | 0.99 | 0.99 |
| Oleic acid | 19.80 | 39.60 | 59.41 |
| Polyoxyl 35 Castor Oil | 39.60 | 29.70 | 9.90 |
| Polysorbate 80 | 19.80 | 9.90 | 9.90 |
| Polyethylene glycol 600 | 9.90 | 9.90 | 9.90 |
| Diethylene glycol monoethyl ether | 9.90 | 9.90 | 9.90 |

Compositions of Example 1 to 3 were prepared by dispersing NRC-AN-019 in Oleic acid, followed by the addition of Polyoxyl 35 Castor Oil, Polysorbate 80, Polyethylene glycol 600 and Diethylene glycol monoethyl ether under stirring with the application of heat.

TABLE 2

| Components | Example 4 % (w/w) | Example 5 % (w/w) | Example 6 % (w/w) | Example 7 % (w/w) |
|---|---|---|---|---|
| NRC-AN-019 | 0.99 | 0.99 | 0.99 | 0.99 |
| Oleic acid | 19.80 | 19.80 | 19.80 | 19.80 |
| Polyoxyl 35 Castor Oil | 39.60 | 39.60 | 39.60 | 39.60 |
| Caprylocaproyl polyoxyl-8 glycerides | 19.80 | 0.00 | 0.00 | 0.00 |
| Caprylic glycerides | 0.00 | 19.80 | 0.00 | 0.00 |
| Sorbitan monooleate | 0.00 | 0.00 | 19.80 | 0.00 |
| PEG-6-Glyceryl linoleate | 0.00 | 0.00 | 0.00 | 19.80 |
| Polyethylene glycol 600 | 9.90 | 9.90 | 9.90 | 9.90 |
| Diethylene glycol monoethyl ether | 9.90 | 9.90 | 9.90 | 9.90 |

Compositions of Example 4 to 7 were prepared by dispersing NRC-AN-019 in Oleic acid, followed by the addition of Polyoxyl 35 Castor Oil, respective co-surfactants, Polyethylene glycol 600 and Diethylene glycol monoethyl ether under stirring with the application of heat. The co-surfactants include Caprylocaproyl polyoxyl-8 glycerides, Caprylic glycerides, Sorbitan monooleate and PEG-6-Glyceryl linoleate in an amount of 19.8% w/w respectively from Example 4 to 7.

TABLE 3

| Components | Example 8 % (w/w) | Example 9 % (w/w) | Example 10 % (w/w) |
|---|---|---|---|
| NRC-AN-019 | 0.92 | 0.39 | 0.39 |
| Oleic acid | 45.27 | 45.52 | 45.52 |
| Polyoxyl 35 Castor Oil | 30.69 | 30.86 | 30.86 |
| Polysorbate 80 | 11.51 | 11.57 | 11.57 |
| Ethanol | 7.67 | 7.71 | 7.71 |
| Soyalecithin (30%) | 3.84 | 3.86 | 0.00 |
| Egg lecithin | 0.00 | 0.00 | 3.86 |
| Butylated hydroxyanisole | 0.08 | 0.08 | 0.08 |
| Butylated hydroxytoluene | 0.02 | 0.02 | 0.02 |

Compositions of Example 8 to 10 were prepared by dispersing NRC-AN-019 in a mixture Soyalecithin, and Oleic acid, followed by the addition of Polyoxyl 35 Castor Oil, Ethanol and Polysorbate 80 under stirring at room temperature. Antioxidants were added to the above mixture. Soyalecithin is replaced with Egg lecithin in Example 10.

TABLE 4

| Components | Example 11 % (w/w) | Example 12 % (w/w) | Example 13 % (w/w) | Example 14 % (w/w) |
|---|---|---|---|---|
| NRC-AN-019 | 1.03 | 1.03 | 1.03 | 1.03 |
| Oleic acid | 47.95 | 47.95 | 47.95 | 47.95 |
| Polyoxyl 35 Castor Oil | 32.58 | 24.43 | 20.36 | 16.29 |
| Caprylocaproyl polyoxyl-8 glycerides | 8.14 | 16.29 | 20.36 | 24.43 |
| Polyethylene glycol 600 | 10.18 | 10.18 | 10.18 | 10.18 |
| Butylated hydroxyanisole | 0.08 | 0.08 | 0.08 | 0.08 |
| Butylated hydroxytoluene | 0.02 | 0.02 | 0.02 | 0.02 |

TABLE 5

| Components | Example 15 % (w/w) | Example 16 % (w/w) | Example 17 % (w/w) | Example 18 % (w/w) |
|---|---|---|---|---|
| NRC-AN-019 | 1.02 | 1.02 | 1.02 | 1.02 |
| Oleic acid | 47.87 | 47.96 | 48.04 | 46.66 |
| Polyoxyl 35 Castor Oil | 16.32 | 24.44 | 24.42 | 7.87 |
| Caprylocaproyl polyoxyl-8 glycerides | 24.49 | 16.29 | 16.28 | 31.47 |
| Polyethylene glycol 600 | 10.20 | 10.18 | 0.00 | 11.80 |
| Benzyl alcohol | 0.00 | 0.00 | 0.00 | 1.18 |
| Ethanol | 0.00 | 0.00 | 10.14 | 0.00 |
| Butylated hydroxyanisole | 0.08 | 0.08 | 0.08 | 0.00 |
| Butylated hydroxytoluene | 0.02 | 0.02 | 0.02 | 0.00 |

Compositions of Example 11 to 18 were prepared by dispersing NRC-AN-019 with solvent, followed by the addition of lipophilic phase, co-surfactant and surfactant phase under stirring with the application of heat for the intimate mixing until a clear solution was obtained. Butylated hydroxyanisole and Butylated hydroxytoluene were added as antioxidants. Polyethylene glycol 600 was replaced with ethanol in Example 17.

Contemplation of solid discrete dosage forms; compositions of the above formulations were scaled up and filled into capsules.

a) directly filled into hard capsules made up of gelatin and these liquid-filled capsules were sealed using a gelatin band.
b) directly filled into hard capsules made up of hydroxyl propyl methyl cellulose and these liquid-filled capsules were sealed using a hydroxyl propyl methyl cellulose band.
c) adsorbed onto the surface of the Neusilin (magnesium aluminometasilicate) in the ratio of 3:1 (solution phase: Neusilin), followed by easy filling into the hard gelatin capsules.
d) adsorbed onto the surface of Neusilin (magnesium aluminometasilicate) in the ratio of 3:1 (solution phase: Neusilin), followed by easy filling into the hard HPMC capsules.
e) encapsulated into soft gelatin capsules by rotary die process.

TABLE 6

| Components | Example 19 % (w/w) | Example 20 % (w/w) | Example 21 % (w/w) | Example 22 % (w/w) |
|---|---|---|---|---|
| NRC-AN-019 | 1.02 | 1.02 | 1.02 | 1.02 |
| Oleic acid | 47.87 | 47.96 | 48.04 | 46.66 |
| Polyoxyl 35 Castor Oil | 10.32 | 20.44 | 24.42 | 6.33 |
| Caprylocaproyl polyoxyl-8 glycerides | 20.49 | 10.29 | 6.28 | 24.42 |
| Polyethylene glycol 600 | 10.20 | 10.18 | 10.18 | 11.80 |
| Vitamin E | 0.10 | 0.10 | 0.10 | 0.10 |
| Polyvinylpyrrolidone K30 | 8.95 | 8.96 | 8.91 | 8.67 |
| Saccharin | 0.50 | 0.50 | 0.50 | 0.50 |
| Flavor | 0.50 | 0.50 | 0.50 | 0.50 |
| Colorants | 0.05 | 0.05 | 0.05 | 0.05 |

Compositions of Example 19 to 22 were prepared by dispersing NRC-AN-019 with solvent phase, followed by the addition of lipophilic phase, co-surfactant, surfactant phase and Polyvinylpyrrolidone K30 under stirring with the application of heat for the intimate mixing until a clear solution is obtained. Vitamin E was added as antioxidant. Sweetening agents and flavors were present in 0.5%.

TABLE 7

| Components | Example 23 % (w/w) | Example 24 % (w/w) | Example 25 % (w/w) |
| --- | --- | --- | --- |
| NRC-AN-019 | 0.50 | 0.51 | 0.51 |
| Oleic acid | 45.48 | 40.84 | 40.44 |
| Caprylocaproyl polyoxyl-8 glycerides | 23.39 | 10.67 | 23.48 |
| Polyoxyl 35 Castor Oil | 19.15 | 32.04 | 23.48 |
| Polyethylene glycol 600 | 10.82 | 15.28 | 11.43 |
| Saccharin | 0.05 | 0.05 | 0.05 |
| Butylated hydroxy anisole | 0.08 | 0.08 | 0.08 |
| Butylated hydroxy toluene | 0.02 | 0.02 | 0.02 |
| Flavor | 0.51 | 0.51 | 0.51 |

Compositions of Example 23 to 25 were prepared by dispersing NRC-AN-019 with solvent phase, followed by the addition of lipophilic phase, co-surfactant and surfactant phase under stirring with the application of heat for the intimate mixing until a clear solution is obtained. Butylated hydroxyanisole and Butylated hydroxytoluene were added as antioxidants. Sweetening agents and flavors were present in 0.05% and 0.5% respectively.

TABLE 8

| Components | Example 26 % (w/w) | Example 27 % (w/w) | Example 28 % (w/w) |
| --- | --- | --- | --- |
| NRC-AN-019 | 1.02 | 1.02 | 1.03 |
| Oleic acid | 47.96 | 47.48 | 40.44 |
| Caprylocaproyl polyoxyl-8 glycerides | 16.29 | 24.43 | 24.52 |
| Polyoxyl 35 Castor Oil | 24.44 | 16.29 | 24.52 |
| Polyethylene glycol 600 | 9.16 | 10.18 | 8.37 |
| Saccharin | 0.51 | 0.00 | 0.51 |
| Butylated hydroxy anisole | 0.08 | 0.08 | 0.08 |
| Butylated hydroxy toluene | 0.02 | 0.02 | 0.02 |
| Flavor | 0.51 | 0.50 | 0.50 |

Compositions of Example 26 to 28 were prepared by dispersing NRC-AN-019 with solvent, followed by the addition of lipophilic phase, co-surfactant and surfactant phase under stirring with the application of heat for the intimate mixing until a clear solution was obtained. Butylated hydroxyanisole and Butylated hydroxytoluene were added as antioxidants.

TABLE 9

| Components | Example 29 % (w/w) | Example 30 % (w/w) | Example 31 % (w/w) |
| --- | --- | --- | --- |
| NRC-AN-019 | 0.62 | 0.92 | 0.62 |
| Oleic acid | 46.72 | 45.27 | 46.72 |
| Polyoxyl 35 Castor Oil | 23.36 | 30.69 | 23.36 |
| Caprylocaproyl polyoxyl-8 glycerides | 19.47 | 0.00 | 19.47 |
| Polysorbate 80 | 0.00 | 11.51 | 0.00 |
| Ethanol | 0.00 | 0.00 | 9.73 |
| Polyethylene glycol 600 | 9.73 | 7.67 | 0.00 |
| Soyalecithin (30%) | 0.00 | 3.84 | 0.00 |
| Butylated hydroxyanisole | 0.08 | 0.08 | 0.08 |
| Butylated hydroxytoluene | 0.02 | 0.02 | 0.02 |

Composition of Example 29 and 31 was prepared by dispersing NRC-AN-019 with solvent, followed by the addition of lipophilic phase, co-surfactant and surfactant phase under stirring with the application of heat for the intimate mixing until a clear solution was obtained. Butylated hydroxyanisole and Butylated hydroxytoluene were added as antioxidants.

Composition of Example 30 was prepared by dispersing NRC-AN-019 in a mixture Soyalecithin and Oleic acid, followed by the addition of Polyoxyl 35 Castor Oil, Polyethylene glycol 600 and Polysorbate 80 under stirring with the application of heat. Antioxidants were added to the above mixture.

TABLE 10

| Components | Example 32 % (w/w) | Example 33 % (w/w) | Example 34 % (w/w) |
| --- | --- | --- | --- |
| NRC-AN-019 | 1.10 | 5.80 | 0.98 |
| Oleic acid | 46.49 | 19.32 | 44.51 |
| Polyoxyl 35 Castor Oil | 7.88 | 14.49 | 22.63 |
| Caprylocaproyl polyoxyl-8 glycerides | 31.52 | 0.00 | 15.09 |
| Polyethylene glycol 600 | 11.82 | 24.15 | 10.18 |
| Benzyl alcohol | 1.18 | 1.45 | 0.00 |
| Dimethyl acetamide | 0.00 | 5.80 | 6.51 |
| Vitamin E acetate | 0.00 | 14.49 | 0.00 |
| Sodium lauryl sulphate | 0.00 | 4.83 | 0.00 |
| d-alpha-tocopheryl polyethylene glycol 1000 succinate | 0.00 | 9.66 | 0.00 |
| Butylated hydroxyanisole | 0.00 | 0.00 | 0.08 |
| Butylated hydroxytoluene | 0.00 | 0.00 | 0.02 |

Composition of Example 32 was prepared by mixing Oleic acid, Caprylocaproyl polyoxyl-8 glycerides, Polyoxyl 35 Castor Oil, Polyethylene glycol 600 and Benzyl alcohol followed by the addition of NRC-AN-019 under stirring with the application of heat.

Composition of Example 33 was prepared by dissolving some amount of NRC-AN-019 in Dimethyl acetamide, followed by the addition of remaining quantity of NRC-AN-019 in a mixture of Polyoxyl 35 Castor Oil, Benzyl alcohol, polyethylene glycol 600, Sodium lauryl sulphate, d-alpha-tocopheryl polyethylene glycol 1000 succinate and Vitamin E acetate under stirring.

Composition of Example 34 was prepared by dissolving some amount of NRC-AN-019 in Dimethyl acetamide and Polyethylene glycol 600, followed by the addition of remaining quantity of NRC-AN-019 in a mixture of Polyoxyl 35 Castor Oil, Caprylocaproyl polyoxyl-8 glycerides and Oleic acid under stirring with the application of heat. Butylated hydroxyanisole and Butylated hydroxytoluene were added to the above.

Compositions of Example 35 to 43, containing fatty acid along with other lipophilic components as the lipophilic phase.

TABLE 11

| Components | Example 35 % (w/w) | Example 36 % (w/w) | Example 37 % (w/w) | Example 38 % (w/w) |
| --- | --- | --- | --- | --- |
| NRC-AN-019 | 0.51 | 0.50 | 0.51 | 0.50 |
| Ricinoleic acid | 45.69 | 19.90 | 19.04 | 0.00 |

TABLE 11-continued

| Components | Example 35 % (w/w) | Example 36 % (w/w) | Example 37 % (w/w) | Example 38 % (w/w) |
| --- | --- | --- | --- | --- |
| Oleic acid | 0.00 | 0.00 | 10.24 | 19.90 |
| Medium chain triglycerides | 0.00 | 19.90 | 0.00 | 19.90 |
| Linseed oil | 0.00 | 0.00 | 19.04 | 0.00 |
| Glycerol monocaprylocaprate | 9.14 | 9.95 | 0.00 | 9.95 |
| Polysorbate 80 | 0.00 | 4.98 | 0.00 | 4.98 |
| Caprylocaproyl polyoxyl-8 glycerides | 0.00 | 4.98 | 16.38 | 4.98 |
| Polyoxyl 35 Castor Oil | 40.61 | 29.85 | 24.56 | 29.85 |
| Polyethylene glycol 600 | 4.06 | 8.96 | 10.24 | 8.96 |
| Benzyl Alcohol | 0.00 | 1.00 | 0.00 | 1.00 |

Compositions of Example 35 to 38 were prepared by dispersing NRC-AN-019 with solvent phase, followed by the addition of lipophilic phase, co-surfactant and surfactant phase under stirring with the application of heat for the intimate mixing until a clear solution is obtained.

TABLE 12

| Components | Example 39 % (w/w) | Example 40 % (w/w) | Example 41 % (w/w) |
| --- | --- | --- | --- |
| NRC-AN-019 | 1.27 | 0.60 | 0.50 |
| Oleic acid | 23.77 | 27.30 | 0.00 |
| Ricinoleic acid | 0.00 | 0.00 | 35.00 |
| Linseed oil | 0.00 | 0.00 | 10.00 |
| Polyoxyl 35 Castor Oil | 23.77 | 32.00 | 35.00 |
| Sorbitan trioleate | 0.00 | 4.00 | 0.00 |
| Caprylocaproyl polyoxyl-8 glycerides | 15.85 | 8.00 | 0.00 |
| Medium chain triglycerides | 20.86 | 16.00 | 0.00 |
| Glycerol monocaprylocaprate | 0.00 | 0.00 | 10.00 |
| Sodium Lauryl Sulphate | 1.90 | 0.00 | 0.00 |
| Butylated hydroxyanisole | 0.08 | 0.10 | 0.00 |
| Butylated hydroxytoluene | 0.02 | 0.02 | 0.00 |
| Glycerine | 11.89 | 0.00 | 0.00 |
| Benzyl alcohol | 0.59 | 0.00 | 0.00 |
| Polyethylene glycol 300 | 0.00 | 12.00 | 0.00 |
| Polyethylene glycol 600 | 0.00 | 0.00 | 9.50 |

Compositions of Example 39 to 41 and was prepared by dispersing NRC-AN-019 with solvent phase, followed by the addition of lipophilic phase, co-surfactant and surfactant phase under stirring with the application of heat for the intimate mixing until a clear solution is obtained. Butylated hydroxyanisole and Butylated hydroxytoluene were added additionally as antioxidants in Example 39 and Example 40.

TABLE 13

| Components | Example 42 % (w/w) | Example 43 % (w/w) |
| --- | --- | --- |
| NRC-AN-019 | 0.50 | 0.5 |
| Oleic acid | 29.85 | 19.90 |
| Capric acid monodiglyceride | 0.00 | 9.95 |
| Sunflower oil and corn oil blend | 9.95 | 0.00 |
| Glycerol monocaprylocaprate | 9.95 | 0.00 |
| Glyceryl monooleate | 0.00 | 19.90 |
| Medium chain triglycerides | 9.95 | 0.00 |
| Polyoxyl 35 Castor Oil | 34.83 | 29.85 |
| Caprylocaproyl polyoxyl-8 glycerides | 0.00 | 4.98 |
| Ethyl oleate | 4.48 | 0.00 |
| Benzyl alcohol | 0.50 | 1.00 |
| Polyethylene glycol 600 | 0.00 | 8.96 |
| Polysorbate 80 | 0.00 | 4.98 |

Composition of Example 42 and 43 were prepared by dispersing NRC-AN-019 with solvent, followed by the addition of lipophilic phase, co-surfactant and surfactant phase under stirring with the application of heat for the intimate mixing until a clear solution was obtained.

Compositions of Example 44 to 46 containing mono-diglycerides as the principal lipophilic phase

TABLE 14

| Components | Example 44 % (w/w) | Example 45 % (w/w) | Example 46 % (w/w) |
| --- | --- | --- | --- |
| NRC-AN-019 | 0.99 | 0.99 | 0.99 |
| Glycerol monocaprylocaprate | 19.80 | 39.60 | 59.41 |
| Polyoxyl 35 Castor Oil | 39.60 | 29.70 | 9.90 |
| Polysorbate 80 | 19.80 | 9.90 | 9.90 |
| Polyethylene glycol 600 | 9.90 | 9.90 | 9.90 |
| Diethylene glycol monoethyl ether | 9.90 | 9.90 | 9.90 |

Compositions of Examples 44 to 46 were prepared according to the procedure described under Example 1 to 3, by replacing the Oleic acid with Glycerol monocaprylocaprate as the lipophilic phase.

TABLE 15

| Components | Example 47 % (w/w) | Example 48 % (w/w) |
| --- | --- | --- |
| NRC-AN-019 | 1.03 | 1.00 |
| Polyoxyl 35 Castor Oil | 30.54 | 0.00 |
| Glycerol monocaprylocaprate | 39.10 | 0.00 |
| Caprylocaproyl polyoxyl-8 glycerides | 14.32 | 12.00 |
| Polyethylene glycol 600 | 0.00 | 30.00 |
| Lactic acid | 4.40 | 0.00 |
| Dimethyl acetamide | 0.00 | 6.00 |
| Vitamin E acetate | 0.00 | 19.00 |
| d-alpha-tocopheryl polyethylene glycol 1000 succinate | 0.00 | 20.00 |
| Ethanol | 10.00 | 12.00 |
| Butylated hydroxyanisole | 0.08 | 0.00 |
| Butylated hydroxytoluene | 0.02 | 0.00 |
| Flavor | 0.51 | 0.00 |

Composition of Example 47 was prepared by dispersing NRC-AN-019 with solvent, followed by the addition of lipophilic phase, co-surfactant and surfactant phase under stirring with the application of heat for the intimate mixing until a clear solution was obtained. Butylated hydroxyanisole and Butylated hydroxytoluene were added as antioxidants. Lactic acid was present in an amount of 4.4% w/w in the composition of Example 47.

Composition of Example 48 was prepared by mixing NRC-AN-019 with Dimethyl acetamide followed by the addition of melted d-alpha-tocopheryl polyethylene glycol 1000 succinate, Polyethylene glycol 600, Caprylocaproyl polyoxyl-8 glycerides, Vitamin E acetate and Ethanol under stirring.

Compositions of Example 49, containing vegetable oils as the principal lipophilic phase

TABLE 16

| Components | Example 49 % (w/w) |
|---|---|
| NRC-AN-019 | 0.99 |
| Olive oil | 19.80 |
| Sunflower oil | 19.80 |
| Canola oil | 19.80 |
| Polyoxyl 35 Castor Oil | 29.70 |
| Caprylocaproyl polyoxyl-8 glycerides | 4.95 |
| Polyethylene glycol 600 | 4.95 |

Composition of Example 49 was prepared by dispersing NRC-AN-019 with solvent, followed by the addition of lipophilic phase, co-surfactant and surfactant phase under stirring with the application of heat for the intimate mixing until a clear solution was obtained.

Compositions of Example 50-52, containing monoglycerides as the principal lipophilic phase

TABLE 17

| Components | Example 50 % (w/w) | Example 51 % (w/w) | Example 52 % (w/w) |
|---|---|---|---|
| NRC-AN-019 | 0.50 | 0.50 | 0.50 |
| Oleic acid | 0.00 | 0.00 | 15.90 |
| Glyceryl monooleate | 44.16 | 30.84 | 30.84 |
| Linseed oil | 0.00 | 15.92 | 0.00 |
| Polyoxyl 35 Castor Oil | 23.77 | 24.62 | 25.24 |
| Caprylocaproyl polyoxyl-8 glycerides | 15.85 | 16.12 | 15.10 |
| Polyethylene glycol 600 | 15.72 | 12.00 | 12.42 |

Composition of Example 50 to 52 were prepared by dispersing NRC-AN-019 with solvent, followed by the addition of lipophilic phase, co-surfactant and surfactant phase under stirring with the application of heat for the intimate mixing until a clear solution was obtained.

TABLE 18

| Components | Comparative Example 1 % (w/w) |
|---|---|
| NRC-AN-019 | 40.00 |
| Polyoxyethylene - Polyoxypropylene Block Copolymer | 20.00 |
| Sodium Lauryl Sulphate | 6.00 |
| Colloidal Silicon Dioxide | 0.40 |
| Crospovidone XL | 20.00 |
| Microcrystalline Cellulose | 12.80 |
| Magnesium Stearate | 0.80 |

Composition of Comparative Example 1 was prepared by the following procedure NRC-AN-019, Sodium Lauryl Sulphate, Polyoxyethylene—Polyoxypropylene Block Copolymer, Crospovidone XL, Microcrystalline Cellulose and Colloidal Silicon Dioxide were taken in required quantity and sieved through 18-mesh sieve in mechanical shifter followed by the mixing procedure in a double cone blender. Then the blended material was loaded into mini roll compactor and the compacted masses were collected in a double lined polybag. The compacts were again compacted in a roller compactor and subsequently shifted through 18-mesh sieve. Further, retains were collected, milled and shifted granules were loaded into roller compactor for compaction. To the above contents required quantity of magnesium stearate was added as lubricant and mixed properly followed by the filling into the capsule shells.

Bioavailability Study for the Compositions in Accordance with the Invention

Four rats (wistar albino, male, weighing 120-180 grams) were divided into two sets of study (two rats in each set) and fasted overnight prior to dosing, but were permitted water ad libitum. The sample preparation and subsequent dilution was made as per protocol with a vehicle, followed by the administration of the sample through oral route. Blood samples were collected by puncturing retero-orbital sinus of the anaesthetized rats (with anesthetic ether) at definite intervals of 15, 30, 60, 120, 240, 360, 480 and 720 minutes post administration. The blood collection was done in pre-filled heparin centrifugation tubes.

The blood samples collected were subjected for the subsequent centrifugation and followed by analytical procedure with the use of LCMS technique. The areas under the blood drug concentration versus time curves are calculated by the trapezoidal rule. The analysis was done with respect to AUC (area under curve), Cmax (maximum concentration) and Tmax (time of maximum concentration).

The average AUC (ng hour/mL), $T_{max}$ (min) and $C_{max}$ (in ng/mL) values from typical trial runs are shown in the following table.

TABLE 19

| Example No. | AUC (ng hour/mL) | $T_{max}$ (hour) | $C_{max}$ (ng/mL) |
|---|---|---|---|
| 16 | 8868.4 | 6.0 | 1043.0 |
| 26 | 6661.6 | 2.0 | 1172.3 |
| 31 | 3097.5 | 8.0 | 643.3 |
| 32 | 11721.5 | 4.0 | 1409.4 |
| 33 | 800.9 | 1.0 | 115.7 |
| 34 | 8478.6 | 6.0 | 976.3 |
| 40 | 3106.8 | 1.0 | 384.6 |
| 48 | 1165.4 | 1.0 | 120.6 |
| Comparative Example 1 (Capsule) | 204.8 | 4.0 | 82.3 |
| Active Pharmaceutical Ingredient | 430.0 | 8.7 | 35.2 |

As will be seen from the above table, compositions in accordance with the present invention exhibit high bioavailability (AUC and Cmax). The aforementioned table gives an account of the improved bioavailability of the invention formulation than that of the capsule dosage form and the API.

Advantages of the Invention a) Lipid based oral solution of a phenylaminopyrimidine derivative for example NRC-AN-019 is prepared which is used as BCR-ABL tyrosine kinase inhibitor for the treatment of Chronic Myeloid Leukemia and against other tumors like head and neck cancer and prostate cancer.
b) The advantage also lies in the attainment of better bioavailability than the tablet and capsule dosage forms.
c) The advantage further encompasses the stability aspects and the formulation is found to be stable throughout the period of the stability study.

d) Patient compliance can be achieved with the oral solution as it is easy to be administered so particularly preferable in pediatric and geriatric patients.
e) Industrial applicability: as ease of manufacturing procedure for the scale-up batches.
f) Particularly till date, no literature has been reported regarding the use of this said derivative in an orally administrable oral solution, which refers to the novelty of the present invention.
g) The formulation provides a therapeutically effective concentration of an extremely water insoluble active ingredient.

We claim:

1. A self-emulsifying pharmaceutical composition for oral administration comprising:
   (a) a therapeutically effective amount of (3,5-bis trifluoromethyl)-N-[4-methyl-3-(4-pyridin-3yl-pyrimidin-2yl amino) phenyl] benzamide (NRC-AN-019) or a pharmaceutically acceptable salt thereof in an amount of from 0.25 to 10% by weight relative to the total weight of the composition;
   (b) a lipophilic phase in an amount of from 12.5 to 65% by weight relative to the total weight of the composition;
   (c) at least one pharmaceutically acceptable surfactant in an amount of from 8 to 60% by weight relative to the total weight of the composition; and
   (d) a pharmaceutically acceptable water miscible solvent in an amount of from 5.5 to 25% by weight relative to the total weight of the composition,
   wherein:
   the lipophilic phase is selected from a triglyceride, a diglyceride, a monoglyceride, a C12 to C22 fatty acid, and a mixture thereof, wherein the triglyceride, diglyceride, or monoglyceride contains C12 to C22 fatty acid residues attached to at least one alcohol group in the glyceride moiety;
   the at least one pharmaceutically acceptable surfactant comprises a polyoxyethylene glycolated vegetable oil;
   the pharmaceutically acceptable water miscible solvent is selected from an α-hydroxy-ω-hydroxy poly(oxy-1,2-ethanediyl) derivative, ethanol or benzyl alcohol.

2. The pharmaceutical composition of claim 1, wherein the lipophilic phase comprises $C_{18}$ unsaturated fatty acid residues, and said $C_{18}$ unsaturated fatty acid residues are present in said lipophilic phase in an amount of at least 20% by weight relative to the total weight of said lipophilic phase.

3. The pharmaceutical composition of claim 1, wherein the lipophilic phase comprises saturated fatty acid residues, and said saturated fatty acid residues are present in said lipophilic phase in an amount of 50% by weight or less based on the total weight of said lipophilic phase.

4. The pharmaceutical composition of claim 1, wherein said at least one surfactant comprises a principal surfactant and one or more co-surfactants.

5. The pharmaceutical composition of claim 4 wherein said co-surfactant is present in an amount of 2 to 60% by weight relative to the total weight of said composition.

6. The pharmaceutical composition of claim 4 wherein said co-surfactant comprises a polyoxyl glyceride.

7. The pharmaceutical composition of claim 4 wherein said co-surfactant is present in an amount of 5 to 45% by weight relative to the total weight of said composition.

8. The pharmaceutical composition of claim 4 wherein said co-surfactant comprises a caprylocaproyl polyoxylglyceride.

9. The pharmaceutical composition of claim 1, wherein said water-miscible solvent acts as a carrier medium for NRC-AN-019.

10. The pharmaceutical composition of claim 1, wherein said water-miscible solvent is polyethylene glycol 600.

11. The pharmaceutical composition of claim 1, which further comprises an antioxidant.

12. The pharmaceutical composition of claim 1, which further comprises a sweetening agent.

13. The pharmaceutical composition of claim 1, which further comprises a flavoring agent.

14. The pharmaceutical composition of claim 1, which is in the form of a solution, a soft gel, or a hard shell capsular formulation.

15. A process for producing a pharmaceutical composition as defined in claim 1 comprising
   mixing NRC-AN-019 with a water miscible solvent,
   addition of a lipophilic phase,
   addition of a surfactant and optionally a co-surfactant, and
   stirring with the application of heat.

16. A method of treating a disease or disorder in a patient comprising administering to said patient a therapeutically-effective amount of a pharmaceutical composition as defined in claim 1.

17. The method of claim 16 wherein said disease or disorder is cancer.

18. The pharmaceutical composition of claim 1 wherein said fatty acid is a mono-unsaturated $C_{12-20}$ fatty acid which is liquid at room temperature.

19. The pharmaceutical composition of claim 1 wherein said fatty acid is (Z)-9-octadecenoic acid.

20. The pharmaceutical composition of claim 1, wherein the lipophilic phase comprises $C_{18}$ unsaturated fatty acid residues, and the $C_{18}$ unsaturated fatty acid residues are present in said lipophilic phase in an amount of at least 40% by weight relative to the total weight of said lipophilic phase.

21. The pharmaceutical composition of claim 1, wherein said at least one surfactant comprises a polyoxyethylene glycolated castor oil.

22. The pharmaceutical composition of claim 1, wherein said at least one surfactant comprises polyoxyl 35 castor oil.

23. The pharmaceutical composition of claim 1, which further comprises an antioxidant, which antioxidant is selected from butyl hydroxyanisole, butyl hydroxytoluene and a mixture thereof.

24. The pharmaceutical composition of claim 1, which further comprises an antioxidant, which antioxidant is a mixture of butyl hydroxyanisole and butyl hydroxytoluene in a ratio from 6:4 to 9:1.

25. The pharmaceutical composition of claim 1, which further comprises an antioxidant, which antioxidant is a mixture of butyl hydroxyanisole and butyl hydroxytoluene in a ratio from 7:3 to 8:2.

26. The pharmaceutical composition of claim 1, which further comprises a sweetening agent, which sweetening agent is saccharin.

27. The pharmaceutical composition of claim 1, which further comprises a sweetening agent, which sweetening agent is saccharin in an amount from 0.1% by weight to 10% by weight relative to the total weight of said composition.

28. The pharmaceutical composition of claim 1, which further comprises a sweetening agent, which sweetening agent is saccharin in an amount from 0.25% by weight to about 5% by weight relative to the total weight of said composition.

29. The pharmaceutical composition of claim 1, which further comprises a flavoring agent, which flavoring agent is selected from oil based flavors, either individually or in combination.

30. The pharmaceutical composition of claim 1, which further comprises a flavoring agent, wherein said flavoring agent is present in an amount from 0.1 wt % to about 10 wt % relative to the total weight of said composition.

31. The pharmaceutical composition of claim 1, which further comprises a flavoring agent, wherein said flavoring agent is present in an amount from 0.25 wt % to 1 wt % relative to the total weight of said composition.

* * * * *